United States Patent [19]
Argo

[11] Patent Number: 6,096,550
[45] Date of Patent: Aug. 1, 2000

[54] METHOD OF TESTING A MATERIAL WITHOUT THE USE OF ANIMALS TO DETERMINE THE POTENTIAL OF THE MATERIAL TO HARM ANIMAL OR HUMAN TISSUE

[76] Inventor: Brian P. Argo, 1750 Edna St., Tracy, Calif. 95376

[21] Appl. No.: 09/070,449

[22] Filed: Apr. 30, 1998

[51] Int. Cl.$^7$ .................................................. G01N 31/00
[52] U.S. Cl. .................................... 436/5; 436/6; 436/71; 436/86; 436/166; 422/82.09; 422/82.11
[58] Field of Search .................................... 436/5, 6, 164, 436/71, 86, 166; 422/53, 55, 57, 82.05, 82.11

[56] References Cited

U.S. PATENT DOCUMENTS 5,411,888  5/1995  Gordon et al. .

OTHER PUBLICATIONS

Chemical Abstracts (Columbus, OH) Abstract No. CA122:2844, Dannenberg et al., Altern. Methods Toxicol. (1994), 10 (In Vitro Skin Toxicology: Irritation, Phototoxicity, Sensitization), pp. 351–366, 1994.
Chemical Abstracts (Columbus, OH) Abstract No. CA121:170775, Levy et al., Skin Pharmacol. (1994), 7(4), pp. 231–236, 1994.
Pezron et al., J. Colloid Interface Sci. (1996), 180(1), pp. 285–289, 1996.
Molecular Monolayers and Films, J.D. Swalen et al, Langmuir, 1987, 3, pp. 932–950.
Supported Membranes: Scientific and Practical Applications, E. Sackmann, Science, Jan. 5, 1996, vol. 271, pp. 43–48.
Influence of Anchor Lipids on the Homegeniety and Mobility of Lipid Bilayers on Thin Polymer Films, D. Beyer et al. Angew. Chem Int. Ed. Engl. 1996, 35, No. 15, 1682–1685.
Investigation of Polymer Thin Films Using Surface Plasmon Modes and Optical Waveguide Modes, E.F. Oust et al, TRIP, vol. 2, No. 9, Sep., 1994, pp. 313–323.
Integrated Optics for the Characterization of Photoreactive Organic Thin Films, W. Knoll, Pure's Appl. Chem., vol. 67, No. 1, pp. 87–94, 1995.
Polymer Thin Films and Interfaces Characterized With Evanescent Light, W. Knoll, Makromol. Chem. 192, No. 12, Dec. 1991, pp. 2827–2856.

*Primary Examiner*—Jan Ludlow
*Attorney, Agent, or Firm*—Thomas R. Lampe

[57] ABSTRACT

A method of testing a material without the use of animals to determine the potential of the material to harm human or animal cells due to contact includes forming a biomembrane having at least some constituent matter of human or animal tissue, applying a quantity of material to the membrane, maintaining the biomembrane and quantity of material in contact for a period of time, and monitoring the change in the physical properties of the biomembrane caused by the quantity of material.

33 Claims, 11 Drawing Sheets

METHOD OF TESTING A MATERIAL WITHOUT THE USE OF ANIMALS TO DETERMINE THE POTENTIAL OF THE MATERIAL TO HARM ANIMAL OR HUMAN TISSUE

TECHNICAL FIELD

This invention relates to a method of testing a consumer product or other material to determine the potential of the material for causing harm when brought into contact with human or animal skin or eyes. The testing procedure is carried out without the use of animals.

BACKGROUND OF THE INVENTION

A number of testing procedures exist to determine the safety of consumer products and other materials with respect to human skin and eyes. Skin and eye safety data are required by various government agencies for many types of materials. Even when not mandated by law, most companies conduct tests to ensure the safety of many types of products.

A number of methods are known in the prior art and employed for estimating dermal and ocular corrosivity of products. Quite commonly such tests involve the use of live animals, primarily white albino New Zealand rabbits.

Problems inherent in animal testing include intra-laboratory variability in scoring and handling, variation in individual rabbit (or other animal) responses, variation in application of test compound and occlusive seal, and variation in sex and age of animals. In addition, the most common animal tests tend to overpredict corrosivity as applied to humans. Some persons criticize the use of animal testing in general on moral or ethical grounds.

Computer modeling has also been employed in some instances as a predictive tool for toxicology. Modeling has only been successfully used for a very few specific applications and only predicts corrosivity/irritation, not the degree thereof.

Diffusion tests utilizing excised animal skin or corneas has also been employed. In such tests, permeability is measured through skin or cornea. One test involving bovine ocular and cornea permeability utilizes a two chamber apparatus wherein one chamber contains a material such as a detergent solution or other compound and the other chamber contains a dye. The dye transfer through the cornea is observed and follow-up pathology measurement of the cornea cells takes place as well. Utilizing this approach, animals are destroyed and animal to animal variability adversely affects the accuracy of the test.

Another prior art test is based on the cytotoxicity of cultured cells. In this approach cells are exposed to solutions or individual compounds for a specified period of time. Dye is then applied which is absorbed into dead or ruptured cells. The effect of the dye on the cells is evaluated visually. This test does not continuously measure the rate at which cellular material is destroyed or the rate that cleaning compounds or other materials adsorb to cellular material during the corrosion process.

Another known approach involves synthetic biomembrane analysis. Biomolecules which make up biomembranes have been studied for skin corrosivity generally for many years and a relationship exists between soap and detergent denaturing and swelling of keratin, the primary protein found in skin, and in vivo dermatitis. These techniques are much like those employed in the cytotoxicity studies discussed above and involve evaluating the biomolecules under a microscope one by one following exposure.

U.S. Pat. No. 5,411,888, issued May 2, 1995, discloses a non-animal testing approach for the measurement of corrosivity of chemicals which essentially is an expansion or elaboration of the biomembrane technique just described. In one approach disclosed in the patent, corrosivity is evaluated by measuring the time required for the test substance to transit a biobarrier that mimics human skin or membranes or the time required to cause a component of such biobarrier to break down and transit the membrane. The invention also envisions alternative approaches which involve series of layers of dyes and corrosive-resistant materials coated onto microspheres or test strips.

The biobarrier suggested by U.S. Pat. No. 5,411,888 is comprised of keratin that has been dissolved in ethylene glycol and cellulose or other materials. While the patent discloses cholesterol as an optional ingredient, it does not disclose how one would make a biomembrane that includes cholesterol or any phospholipids. The test cannot readily distinguish between rapid reactions and distinctions in reaction speeds are critical to the design of safer consumer products and other types of materials, insofar as ocular and skin corrosivity is concerned. Also, ethylene glycol, cellulose and other materials employed in the test may have interfering side reactions with chemicals under study.

DISCLOSURE OF INVENTION

The present invention relates to a method of testing a material without the use of animals to determine the potential of the material to harm human or animal cells due to contact. The procedure is particularly useful to determine the ocular and skin corrosivity of a material.

Utilizing the method of the present invention actual constituent components found in human or animal eye and skin tissue are utilized. No animals need be destroyed and the negative impact on testing accuracy due to animal to animal variability and other factors is eliminated.

The testing approach of the present invention enables the person or persons conducting the test to measure the rate at which cellular material is destroyed and the rate at which materials such as cleaning compounds adsorb to cellular material during the corrosion process.

Also, according to the teachings of the present invention, a biofilm is produced that closely replicates skin membrane consisting of both the protein cytoskeleton and lipids. The films employed could also be modified to contain keratin in greater or lesser quantities to approximate older and younger skin. The membranes found in the human eye can also be readily approximated. Compared to prior art approaches, the techniques employed in the present invention lend themselves to far more reproducible results since the biomembranes may be built by applying films of specified composition one molecule thick at a time. Finally, a very accurate measurement of reaction speeds is obtained.

The present method includes the step of forming a biomembrane having at least some constituent matter of human or animal tissue.

A quantity of material is applied to the biomembrane, with the biomembrane and quantity of material maintained in contact for a period of time after applying the quantity of material to the biomembrane.

The method also includes the step of monitoring changes in the physical characteristics of the biomembrane caused by the quantity of material during the period of time.

The step of forming the membrane comprises depositing at least one layer including protein or lipid matter on a substrate. According to the preferred approach disclosed herein, the step of monitoring changes in the physical characteristics of the biomembrane comprises utilizing a surface plasmon spectrometer to measure changes in the thickness of the biomembrane.

Other features, advantages, and objects of the present invention will become apparent with reference to the following description and accompanying drawings.

MODES FOR CARRYING OUT THE INVENTION

Figure 1:
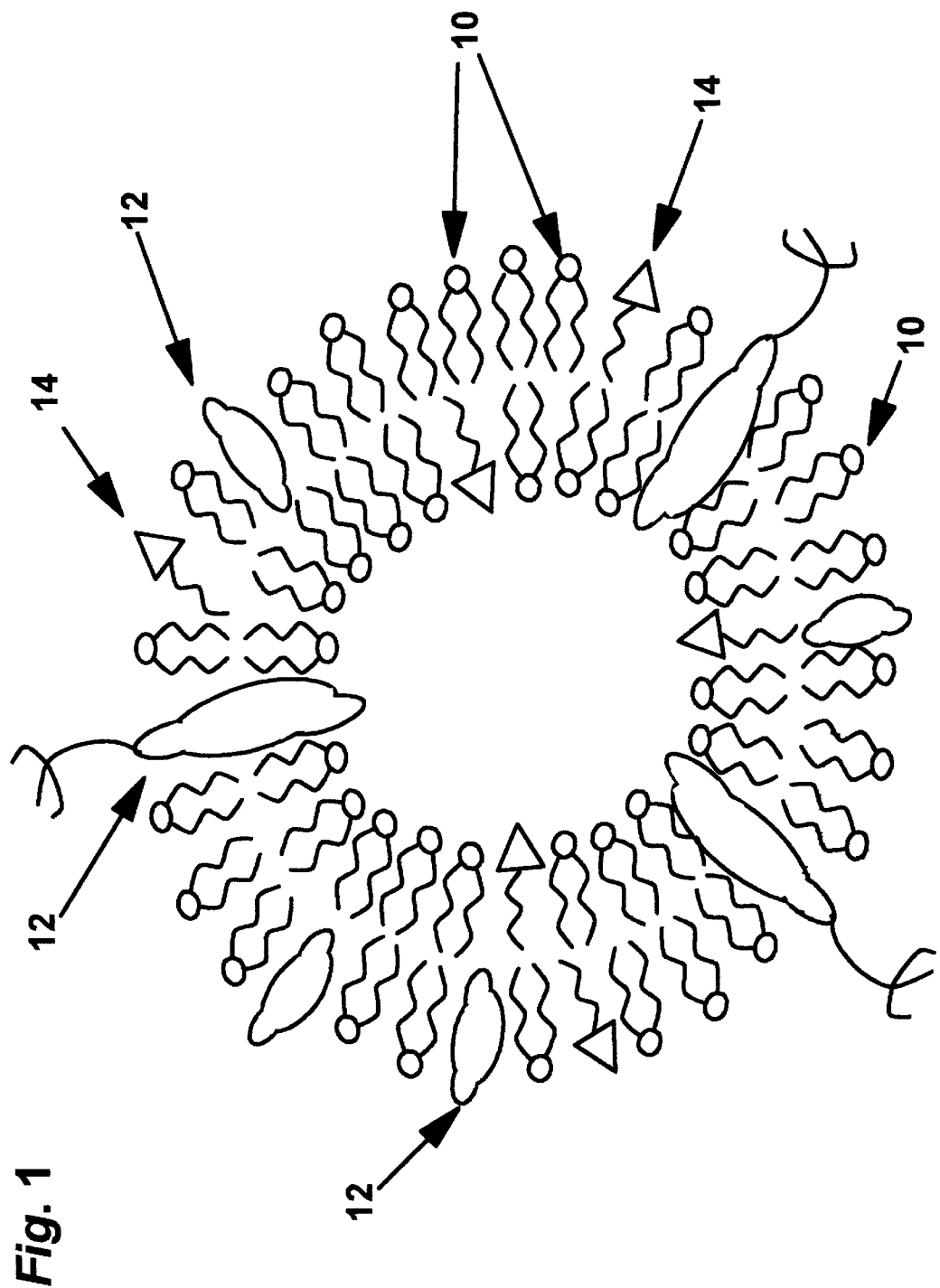
FIG. 1 is a schematic representation of a simplified cell membrane including protein, lipid matter and cholesterol.

FIG. 1 is a schematic representation of a generic cell membrane. Human skin cellular walls are made up of varying and various ingredients and are extremely complex. However, the vast majority of material in every cell wall is made up of lipid matter 10 and protein 12. The illustrated cell membrane also includes cholesterol 14. Cells differ in their make up primarily by the type of lipid, the type of protein, and the type of cholesterol. Since these materials can be organized in the laboratory, human tissue for test purposes can essentially be synthesized. Different human cell walls can be synthesized by varying the lipid and protein types as well as by possibly adding other constituent matter of a human cell wall such as cholesterol.

Fabrications of monolayer phospholipid-protein membranes and such materials and/or techniques for making same are set forth in the following publications: Molecular Monolayers and Films, J. D. Swalen et al, LANGMUIR, 1987, 3, pages 932–950; Supported Membranes: Scientific and Practical Applications, E. Sackmann, SCIENCE, Jan. 5, 1996, Volume 271, pages 43–48; and Influence Of Anchor Lipids On The Homegeniety And Mobility Of Lipid Bilayers On Thin Polymer Films, D. Beyer et al, Angew. Chem Int. Ed. Engl. 1996, 35, No. 15, 1682–1685.

A known apparatus for forming thin films is the Langmuir-Blodgett trough and Langmuir-Blodgett films consist of mono-molecular layers stacked sequentially onto a solid substrate. One of the preferred embodiments of the present invention utilizes the Langmuir-Blodgett technique to form a biomembrane having constituent matter of human or animal tissue which is subsequently tested to determine the potential of a material to harm human or animal cells due to contact. Other techniques of biomembrane fabrication are possible however, and alternative techniques are noted below.

Figure 2:
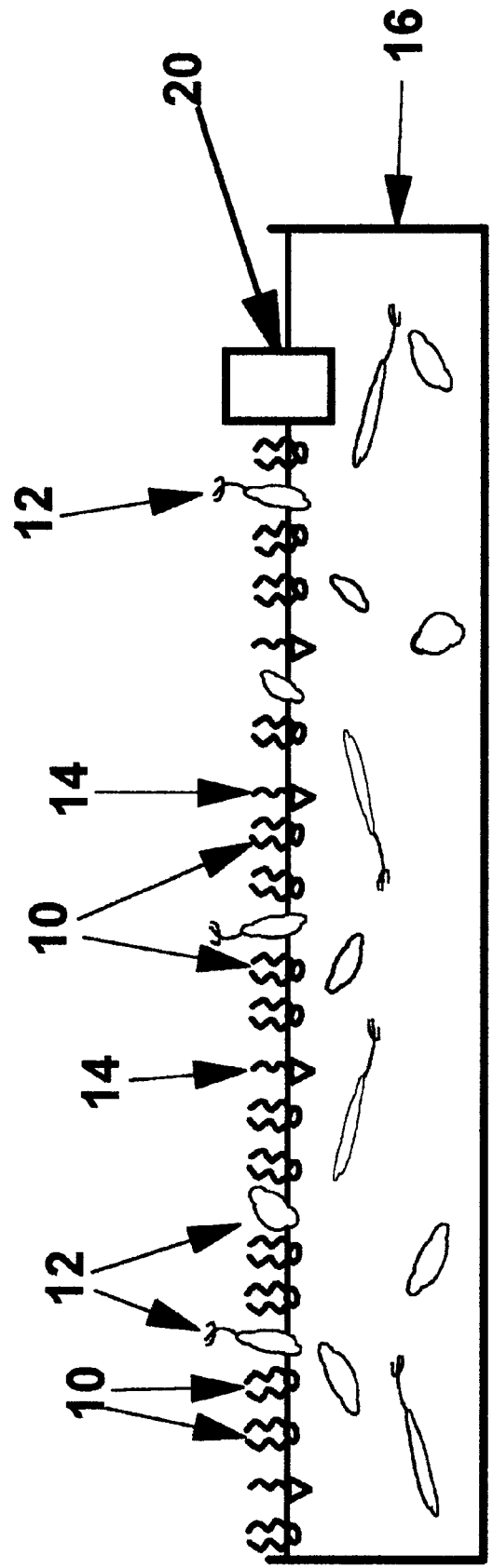
FIG. 2 is a schematic representation of a Langmuir-Blodgett trough and matter contained in the trough employed when forming a biofilm in accordance with the teachings of the present invention.

FIG. 2 shows a Langmuir-Blodgett trough 16 filled with a solution 18 including protein 12, having a film interface thereon including phospholipid matter 10 and cholesterol 14. As is conventional, the trough 16 includes a movable barrier 20 employed to maintain a constant surface pressure at the film interface. In the practice of the present invention, the trough 16 can be used for two distinct applications: (1) a protein phospholipid layer and (2) a phospholipid layer. The mixed layer is formed by dissolving the protein in water and then using a spreading solution with phospholipids and cholesterol to form the mixed layer. A separate trough will be used with the phospholipids/cholesterol layer to complete the bilayer.

Figure 3:
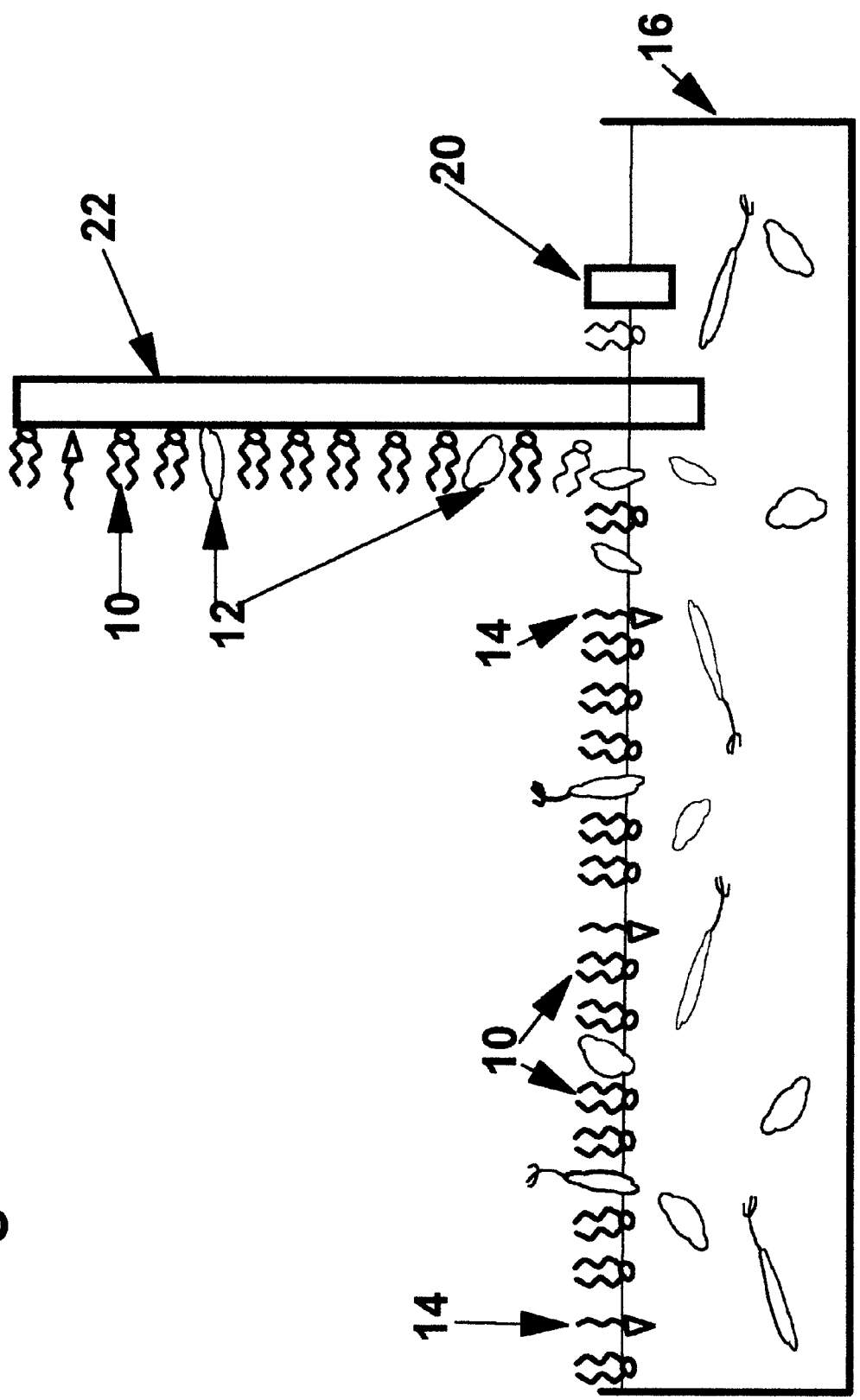
FIG. 3 illustrates a substrate being withdrawn from the Langmuir-Blodgett trough with a single layer of biofilm attached to a hydrophilic substrate.
Figure 5:
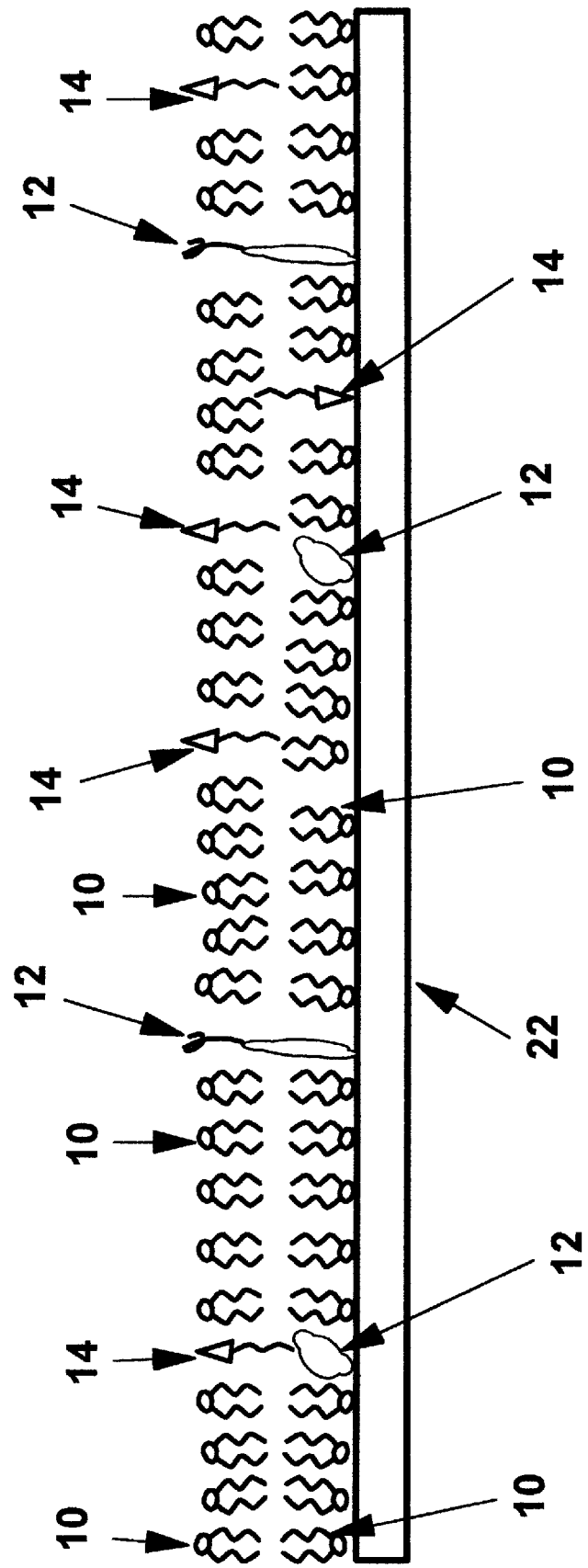
FIG. 5 is a view similar to FIG. 4 but illustrating a biomembrane resulting from a second immersion exposing the first applied layer to a pure lipid film interface.

Referring now to FIGS. 3 and 5, the Langmuir-Blodgett trough 16 can be used to create a biofilm by simply dipping a clean hydrophilic substrate through the protein/phospholipid/cholesterol system, then dipping the surface through a phospholipid/cholesterol system. In FIG. 3 the substrate is shown partially immersed in the trough solution and is designated by reference numeral 22.

The substrate 22 is suitably made of glass with a thin gold coating. Glass and metal are commonly called high energy or water loving or hydrophilic surfaces. Generally, either an adsorbed polymer or protein or a self assembled thin film made from siloxane can be added as a primer coating to change the surface from water loving to water hating or hydrophobic. Alternatively, a hydrophilic terminal group can be added to the thiol to maintain hydrophilicity. In the case of metal surfaces alkyl terminated thiols can be employed. Primer coatings are used for systems in which absorption of oils, fatty acids or other hydrophobic moieties is desired.

The hydrophilic substrate 22 is then dipped into the phospholipid interface in the trough. Barrier 20 moves to maintain a constant surface pressure during the dipping process through a feedback control mechanism and a film that is only one molecule thick can then be applied to the substrate surface.

Figure 4:
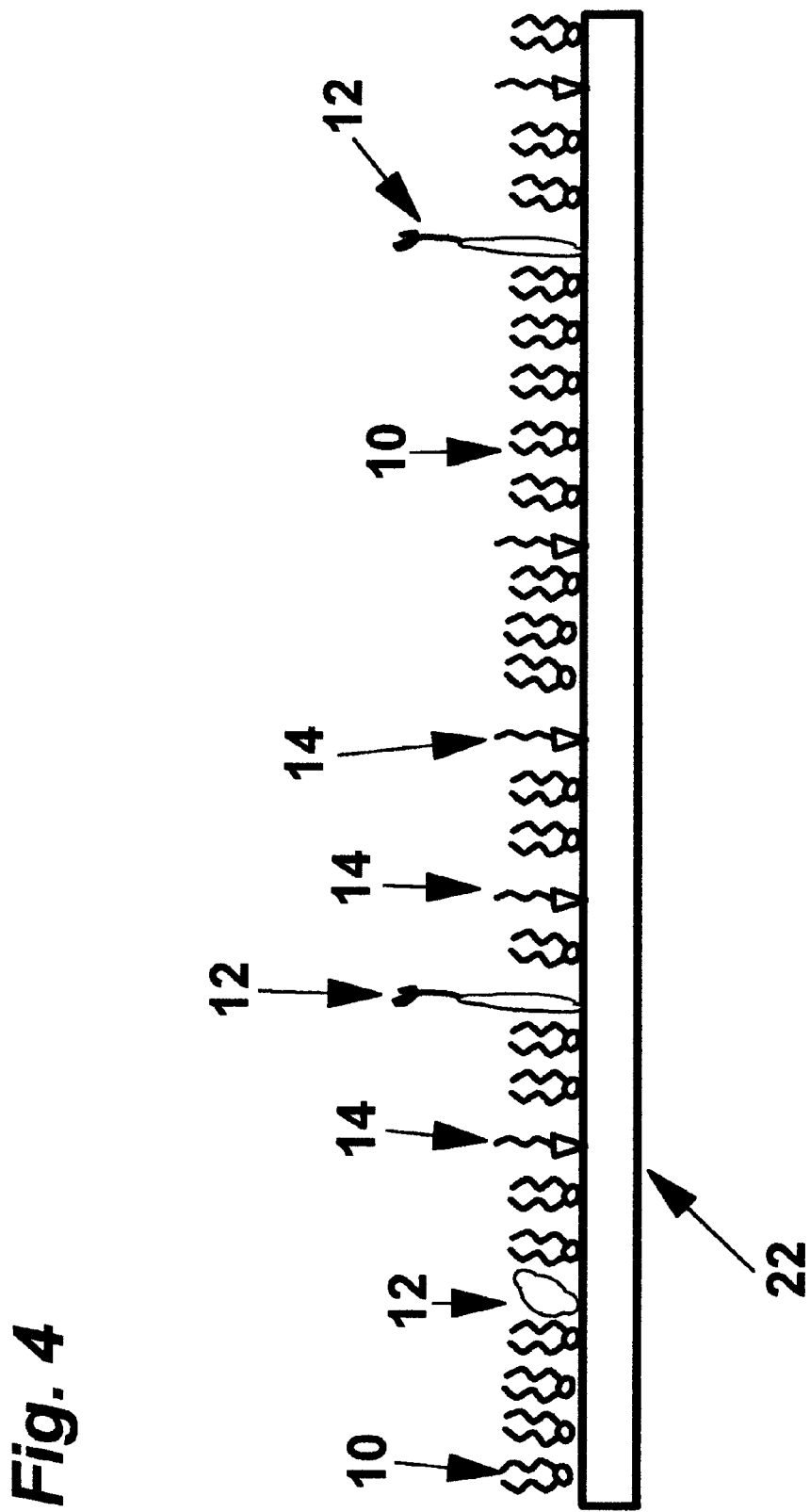
FIG. 4 is a schematic representation of the substrate and a biomembrane comprised of a single layer of biofilm located thereon.

FIG. 3 shows the substrate 22 in the final stage of being removed from the trough after being dipped in the solution and FIG. 4 shows the substrate 22 with a reconstituted partial cell membrane on the surface thereof, the surface having been converted from a hydrophilic surface to a hydrophobic surface. The material at the surface of the solution in the trough contains proteins, phospholipid matter and cholesterol.

FIG. 5 shows a reconstituted complete cell membrane on a hydrophilic substrate. This structure results from a second dip into a Langmuir-Blodgett trough having a phospholipid/cholesterol system in solution therein. This procedure can be repeated many, even hundreds of times if necessary or desired for test accuracy.

Figure 6:
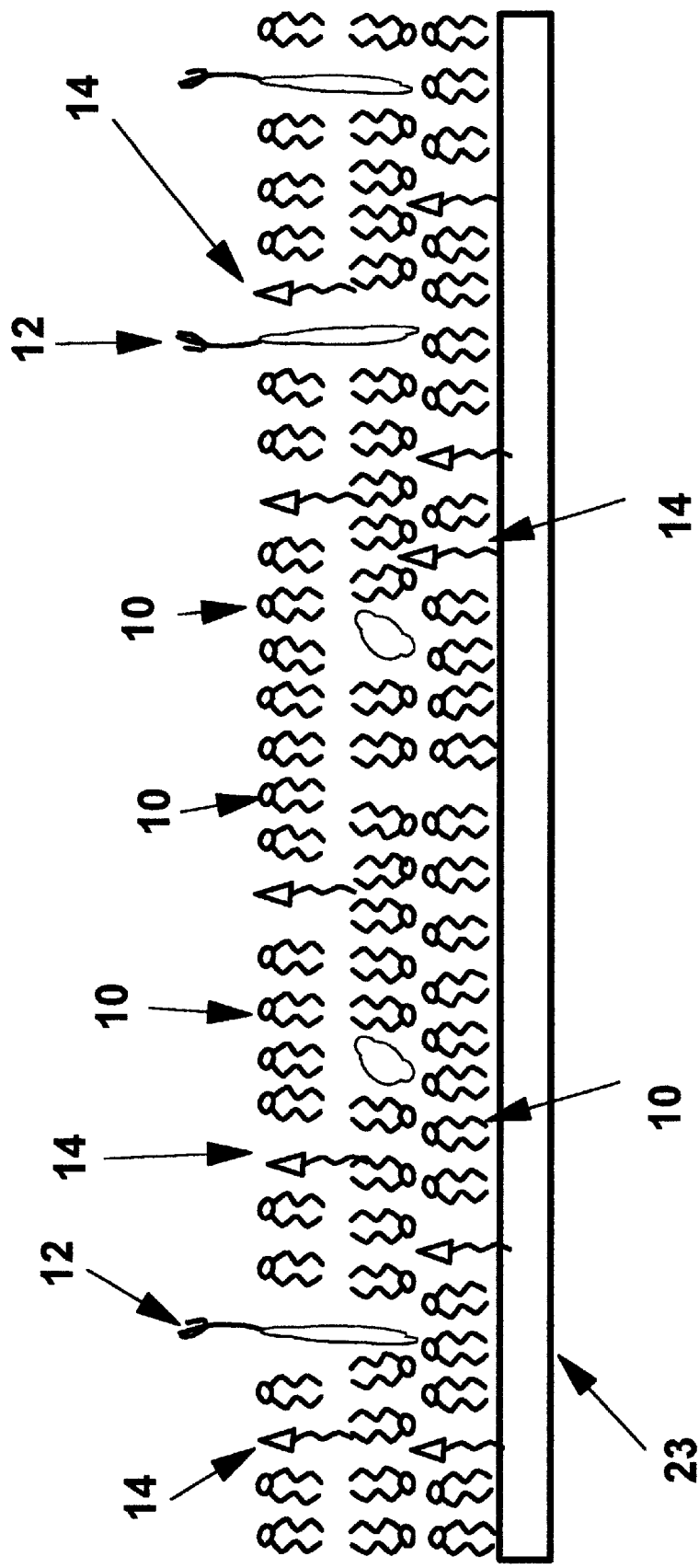
FIG. 6 is a view similar to FIGS. 4 and 5 but illustrating a biomembrane on the substrate wherein the surface of the substrate was hydrophobic during an initial immersion into the trough followed by two subsequent immersions.

A similar procedure can be carried out on hydrophobic surfaces, as shown in FIG. 6. The only difference is that one would start by dipping the hydrophobic surface of the substrate 23 into a bath with a monolayer of phospholipid/cholesterol to convert the surface from hydrophobic to hydrophilic. One would then follow the same steps outlined above with respect to the hydrophilic surface. The resultant structure is illustrated in FIG. 6 and incorporates 3 layers.

Figure 7:
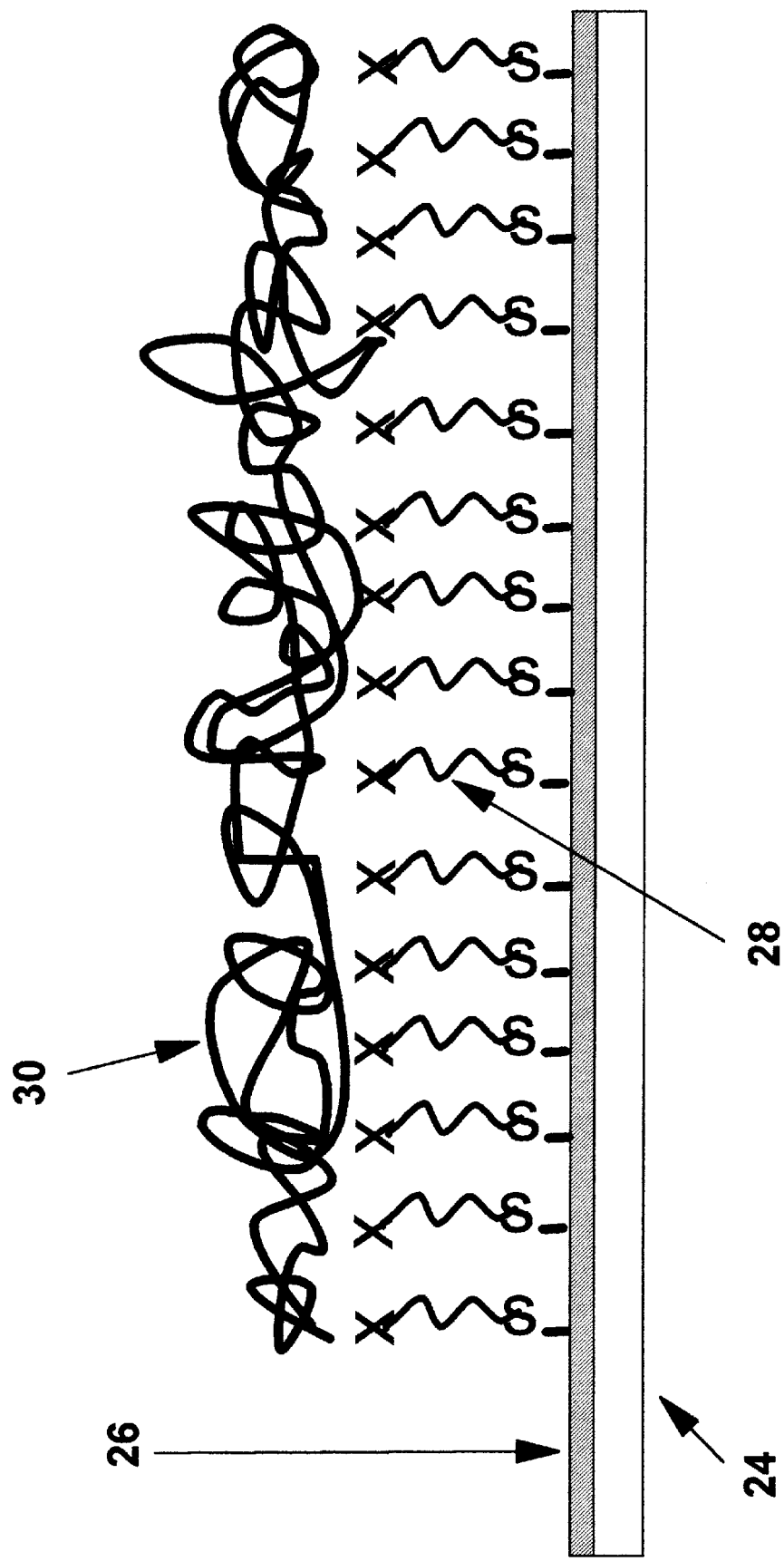
FIG. 7 is a representation of a polymer film attached to a self-assembled-monolayer.

Referring now to FIG. 7, it is also possible to increase the fluidity of the test surface by building a polymer film. Although there are a number of ways to carry out such a procedure, the following known process of building a polymer film has found acceptance. First, metal, for example gold, is evaporated onto a glass slide 24 to form a gold layer 26.

Next the metal is exposed to a thiol solution that contains end groups with moities that initiate polymers as shown by the Xs 28. The thiols spontaneously form a self-assembled-monolayer (SAM) through chemisorption. Next, one exposes the SAM to a hydrophilic monomer and allows polymerization to occur on the surface. Polymerization then starts on the thiol SAM and grows into the solution. The polymer is designated in FIG. 7 by reference numeral 30.

Figure 8:
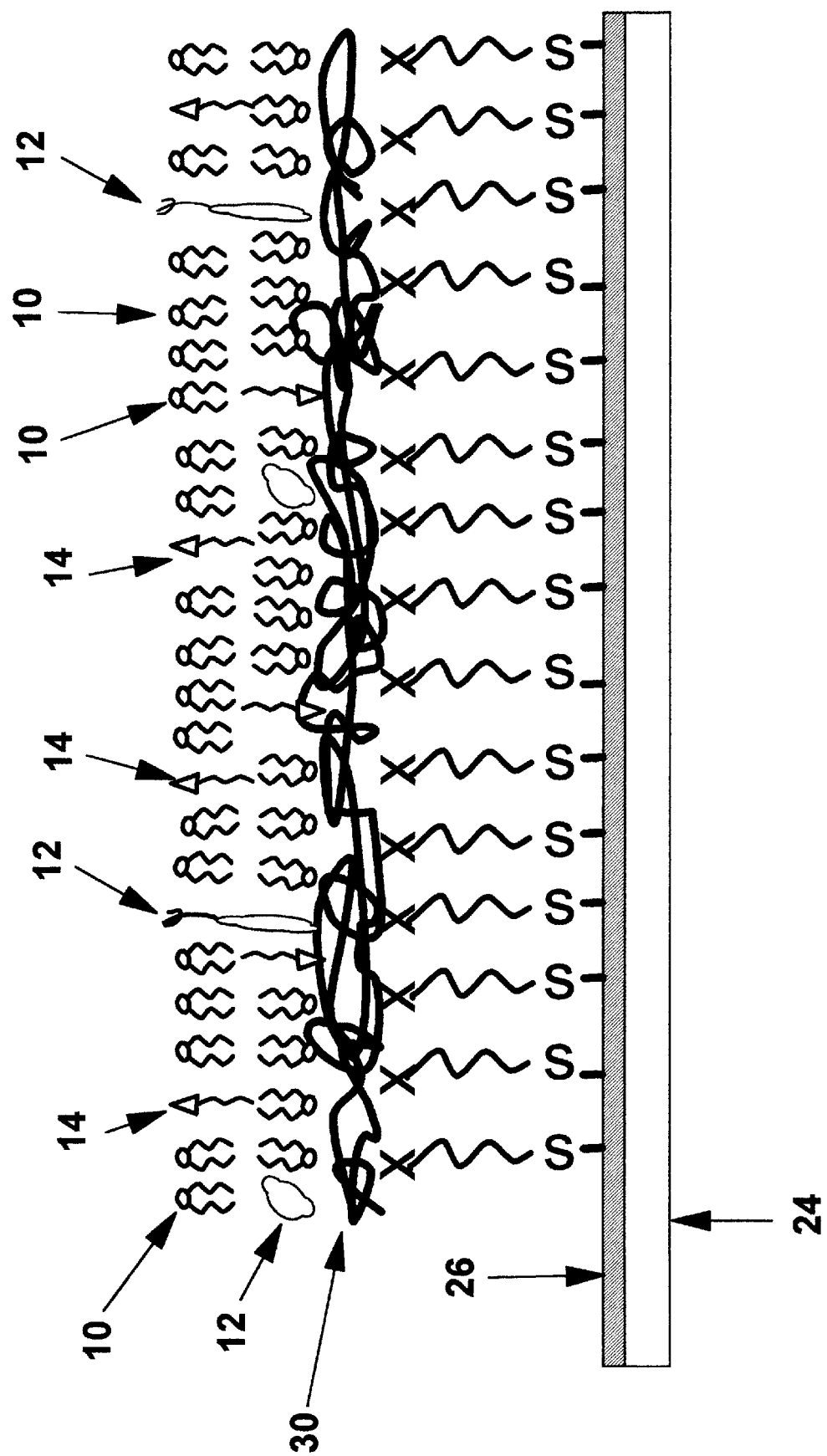
FIG. 8 illustrates the structure resulting after two biofilm layers have been applied to the polymer film of FIG. 7 by immersions of the polymer film into the Langmuir-Blodgett trough or vesicular deposition.

Nature usually has fluid surfaces and this fluidity is thought to be related to the healing process; therefore, utilization of this step may assist in obtaining a correlation to existing animal data and render the use of further animal testing unnecessary. The surface of the structure in FIG. 7 is squishy due to water associated with the polymer groups and flexibility of polymers. Biofilms are then applied utilizing the Langmuir-Blodgett trough as described above and FIG. 8 shows the end result. The end result shown in FIG. 8 can also be produced by physisorption of vesicles.

Figure 9:
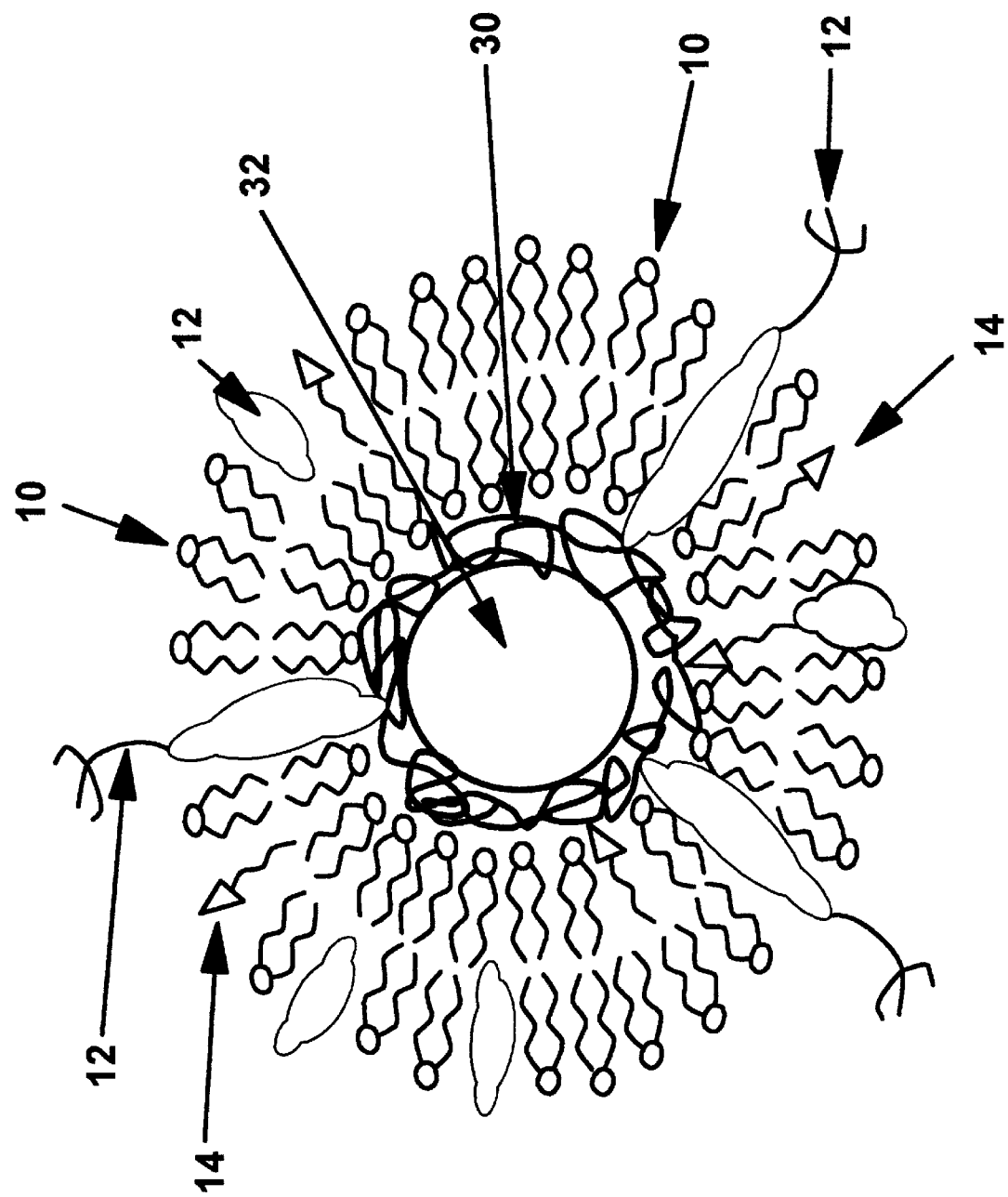
FIG. 9 is a schematic representation of generic cell membrane material attached to a particle substrate.

SAMs and polymer layers can be built on a variety of surfaces. Such surfaces need not be flat. FIG. 9 illustrates a structure including a solid silica sphere 32. Attached to this spherical particulate substrate is polymer 30 also having a generally spherical configuration. A biomembrane consisting of phospholipid matter 10, protein 12 and cholesterol 14 may then be formed on the polymer.

Figure 10:
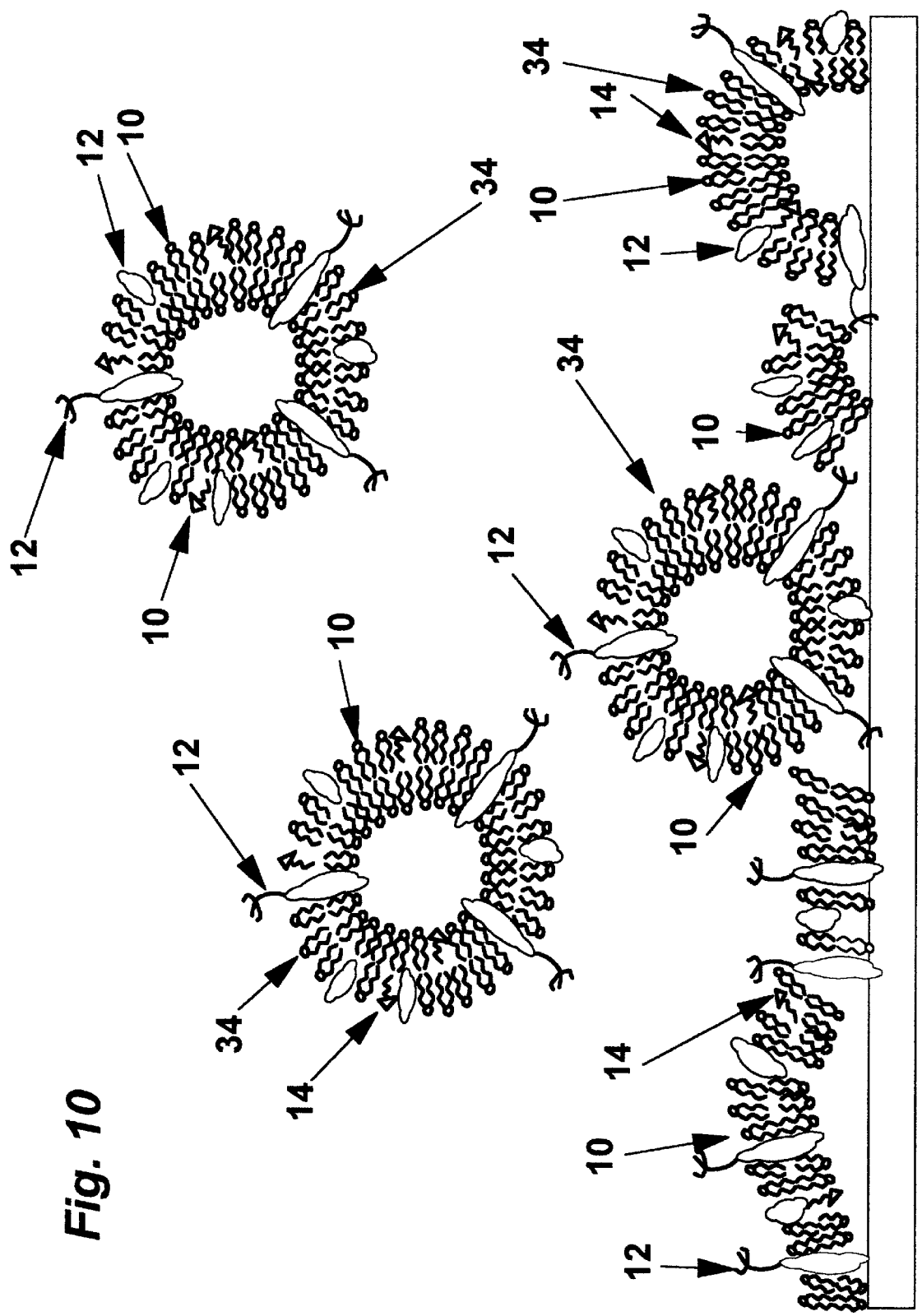
FIG. 10 is a schematic representation of an alternative approach for forming a biofilm in which vesicles are deposited on a substrate in water.

Other approaches may be used to form a biomembrane. In this connection, reference should be had to FIG. 10 wherein a plurality of vesicles 34 are deposited on a substrate 22. The vesicles are reconstituted cell membranes which contain water internally instead of the normal cellular materials. Vesicles can be used to apply biofilms on a variety of surfaces. These typically are deposited on a surface, then allowed to dry.

Known biofilm formation techniques may be employed other than those specifically described above, including self-assembly, physisorption, chemisorption and Langmuir-Schaefer techniques.

After the biomembrane having constituent matter of human tissue has been formed, a quantity of material to be tested is applied to the biomembrane. Such material may, for example, be a consumer product such as a cleanser, detergent or ingredients. The present invention is applicable to test virtually any material to determine its potential for harming human or animal tissue.

The quantity of material is maintained in contact with the biomembrane for a period of time.

When practicing the invention the degradation caused to the biomembrane by the quantity of material during the period of time is monitored. More specifically, the preferred approach now to be described monitors the degradation of the biomembrane by measuring changes in the thickness of the biomembrane occurring during the period of contact between the material and biomembrane.

Figure 11:
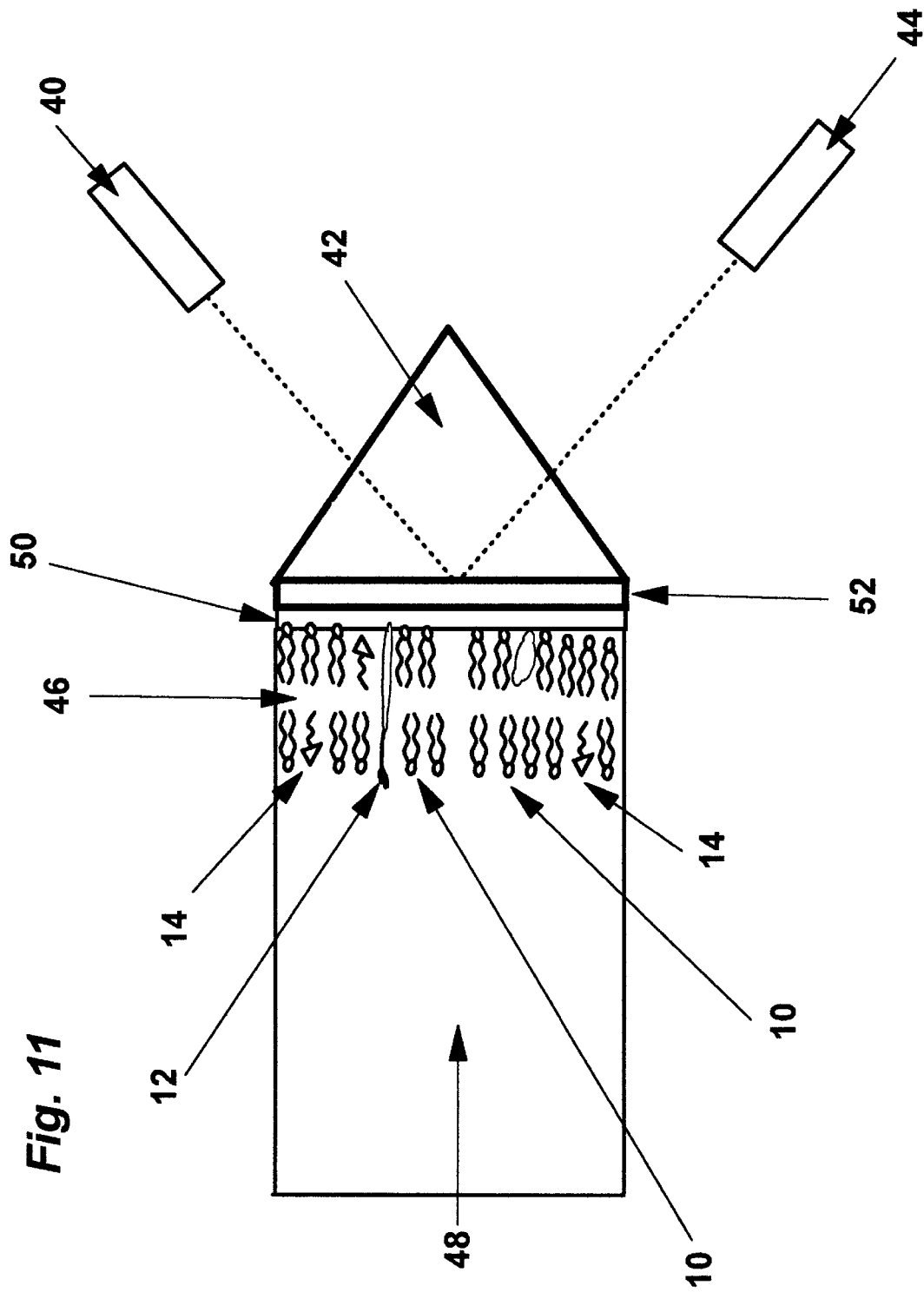
FIG. 11 is a diagrammatic representation of a surface plasmon spectrometer employed to detect and quantify degradation of a biofilm.

FIG. 11 illustrates in schematic fashion the use of a surface plasmon spectrometer to measure degradation of a biomembrane. The surface plasmon spectrometer uses light targeted onto a metal surface to create an evanescent wave or a probing electron (aka the surface plasmon effect). When using a laser the angle at which the evanescent wave is maximized is a function of the thickness of the material covering the surface, and slight changes in that angle provide highly accurate measurement of changes in the thickness or refractive index of the film.

The surface plasmon spectrometer is especially useful due to its ability to measure the rate of change of the film. Since the surface plasmon spectrometer only measures solid state materials or film materials attached to a solid surface, it can be used to measure degradation of surfaces exposed to various chemical compounds. Finally, the surface plasmon spectrometer can be used to produce actual images of the surface by splitting the beam or rastering the laser across the surface. For general information concerning surface plasmon and evanescent light techniques, reference may be had to the following publications: Investigation of Polymer Thin Films Using Surface Plasmon Modes and Optical Waveguide Modes, E. F. Oust et al, TRIP, Volume 2, No. 9, September, 1994, pages 313–323; Integrated optics For The Characterization Of Photoreactive Organic Thin Films, W. Knoll, Pure & Appl. Chem., Volume 67, No. 1, pages 87–94, 1995; and Polymer Thin Films And Interfaces Characterized With Evanescent Light, W. Knoll, Makromol. Chem. 192, No. 12, December, 1991, pages 2827–2856.

In FIG. 11 the schematically illustrated structural components include a laser 40, a glass prism 42 and a detector 44.

A reconstituted complete biomembrane 46 is located in the sample chamber 48 of the surface plasmon spectrometer, the substrate (including a metal layer 50 and a glass slide 52) being located between the glass prism 42 and the sample chamber.

Utilizing the teachings of the present invention, physical characteristics of biofilms other than thickness may be utilized to measure changes made to the biomembrane by materials, including such properties as refractive index, mass permeability, fluidity, optics, electrical conductivity, order, and so forth.

In a case where a test sample incorporates itself into the biofilm, the surface plasmon spectrometer equipment can be used with optical wave guide modes. Optical wave guide modes allow independent measurement of both index of refraction and material thickness but have the disadvantage of requiring thicker sample sizes.

Rather than utilizing surface plasmon spectroscopy to measure changes, other techniques may be employed such as Fourier transform infrared spectroscopy, ellipsometry, second harmonic generation, microprobe microscopy (AFM, STM, FFM, etc.), UV/visible spectroscopy, contact angle measurement, X-ray diffraction, X-ray reflection, neutron reflection, voltometry microfluorometry, nuclear magnetic resonance, light scattering (particulate suspensions), neutron scattering, surface force balance, X-ray photoelectron spectroscopy, secondary ion mass spectrometry, and spectroscopic ellipsometry. For a general introduction to such techniques, referral may be had to An Introduction to Ultrathin Organic Films, A. Ullman, Academic Press, San Diego, Calif., 1991.

What is claimed is:

1. A method of testing a material without the use of animals to determine the potential of the material to harm human or animal tissue, said method comprising the steps of:

forming a biomembrane comprised of at least one biofilm layer by depositing at least one biofilm layer on a substrate, said at least one biofilm layer having physical characteristics of human or animal tissue and including at least some constituent matter of human or animal tissue;

applying a quantity of material to said biomembrane;

maintaining said biomembrane and said quantity of material in contact for a period of time after applying said quantity of material to said biomembrane; and monitoring the condition of the biomembrane during said period of time to detect any change in at least one physical characteristic of said biomembrane caused by said quantity of material during said period of time, said step of monitoring the condition of the biomembrane comprising measuring any chances in the thickness of said biomembrane occurring during said period of time.

2. The method according to claim 1 wherein a plurality of biofilm layers are sequentially deposited on said substrate.

3. The method according to claim 1 wherein changes in the thickness of said biomembrane are measured by a surface plasmon spectrometer.

4. The method according to claim 3 wherein the surface plasmon spectrometer measures changes in the refractive index of the biomembrane.

5. The method according to claim 4 wherein changes in the refractive index of the biomembrane are measured on a substantially continuous basis.

6. The method according to claim 1 wherein said biomembrane includes protein or lipid matter.

7. The method according to claim 6 wherein said lipid matter is phospholipid matter.

8. The method according to claim 1 wherein changes in the thickness of said biomembrane are measured on a substantially continuous basis.

9. The method according to claim 1 wherein protein, lipid matter and cholesterol are incorporated in said biomembrane during forming of said biomembrane.

10. The method according to claim 1 wherein said at least one biofilm layer is deposited on the substrate by bringing a plurality of vesicles including biofilm material into engagement with a substrate, and causing biofilm deposition on the substrate from said plurality of vesicles.

11. The method according to claim 1 wherein said biomembrane is formed on a polymer film.

12. A method of testing a material without the use of animals to determine the potential of the material to harm human or animal tissue, said method comprising the steps of:

forming a biomembrane having at least some constituent matter of human or animal tissue;

applying a quantity of material to said biomembrane;

maintaining said biomembrane and said quantity of material in contact for a period of time after applying said quantity of material to said biomembrane; and monitoring the condition of said biomembrane to detect any change in at least one physical characteristic of said biomembrane caused by said quantity of material during said period of time, said step of monitoring the condition of said biomembrane to detect any change in at least one physical characteristic of said biomembrane comprising measuring any change in the thickness of said biomembrane occurring during said period of time, change in the thickness of said biomembrane being measured by a surface plasmon spectrometer.

13. A method of testing a material without the use of animals to determine the potential of the material to harm human or animal tissue, said method comprising the steps of:

forming a biomembrane having at least some constituent matter of human or animal tissue;

applying a quantity of material to said biomembrane;

maintaining said biomembrane and said quantity of material in contact for a period of time after applying said quantity of material to said biomembrane; and monitoring the condition of said biomembrane to detect any change in at least one physical characteristic of said biomembrane caused by said quantity of material during said period of time, said step of forming said biomembrane comprising depositing at least one biofilm layer on a substrate, said at least one biofilm layer at least partially comprised of protein or lipid matter and the step of depositing said at least one biofilm layer on said substrate including passing said substrate through a film interface on a solution and subsequently withdrawing said substrate from said solution with a layer at least partially comprised of protein or lipid matter attached to said substrate, said substrate being passed through the film interface on a solution a plurality of times to sequentially deposit biofilm layers on said substrate and form a biomembrane comprising a plurality of biofilm layers.

14. A method of testing a material without the use of animals to determine the potential of the material to harm human or animal cells, said method comprising the steps of:

forming a biomembrane having at least some constituent matter of human or animal tissue;

applying a quantity of material to said biomembrane;

maintaining said biomembrane and said quantity of material in contact for a period of time after applying said quantity of material to said biomembrane;

monitoring the condition of said biomembrane to detect any change in at least one physical characteristic of said biomembrane caused by said quantity of material during said period of time, said step of forming said biomembrane comprising depositing at least one biofilm layer on a substrate, said at least one biofilm layer being at least partially comprised of protein or lipid matter and the step of depositing said at least one biofilm layer on said substrate including passing said substrate through a film interface on a solution and subsequently withdrawing said substrate from said solution with a layer at least partially comprised of protein or lipid matter attached to said substrate;

incorporating protein in said solution whereby protein is attached to said substrate in said at least one biofilm layer when said substrate is passed through the film interface on said solution; and providing a mixture of protein and lipid matter at said film interface whereby said at least one biofilm layer includes a mixture of protein and lipid matter.

15. A method of testing a material without the use of animals to determine the potential of the material to harm human or animal tissue, said method comprising the steps of:

forming a biomembrane having at least some constituent matter of human or animal tissue;

applying a quantity of material to said biomembrane;

maintaining said biomembrane and said quantity of material in contact for a period of time after applying said quantity of material to said biomembrane;

monitoring the condition of said biomembrane to detect any change in at least one physical characteristic of said biomembrane caused by said quantity of material during said period of time, said step of forming said biomembrane comprising depositing at least one biofilm layer on a substrate, said at least one biofilm layer being at least partially comprised of protein or lipid matter and the step of depositing said at least one biofilm layer on said substrate including passing said substrate through a film interface on a solution and subsequently withdrawing said substrate from said solution with a layer at least partially comprised of protein or lipid matter attached to said substrate;

incorporating protein in said solution whereby protein is attached to said substrate in said at least one biofilm layer when said substrate is passed through the film interface on said solution; and incorporating cholesterol in said solution whereby cholesterol is attached to said substrate in said at least one layer when said substrate is passed through the film interface on said solution.

16. A method of testing a material without the use of animals to determine the potential of the material to harm human or animal tissue, said method comprising the steps of:

forming a biomembrane having at least some constituent matter of human or animal tissue;

applying a quantity of material to said biomembrane;

maintaining said biomembrane and said quantity of material in contact for a period of time after applying said quantity of material to said biomembrane; and monitoring the condition of said biomembrane to detect any change in at least one physical characteristic of said biomembrane caused by said quantity of material during said period of time, said step of forming said biomembrane comprising depositing at least one biofilm layer on a substrate, said at least one biofilm layer being deposited on the substrate by bringing a plurality of vesicles including biofilm material into engagement with a substrate, and causing biofilm deposition on the substrate from said plurality of vesicles.

17. A method of testing of material without the use of animals to determine the potential of the material to harm human or animal tissue, said method comprising the steps of:

forming a biomembrane having at least some constituent matter of human or animal tissue;

applying a quantity of material to said biomembrane;

maintaining said biomembrane and said quantity of material in contact for a period of time after applying said quantity of material to said biomembrane; and monitoring the condition of said biomembrane to detect any change in at least one physical characteristic of said biomembrane caused by said quantity of material during said period of time, said step of forming said biomembrane comprising depositing at least one biofilm layer on a substrate, said at least one biofilm layer being at least partially comprised of protein or lipid matter and the step of depositing said at least one biofilm layer on said substrate including passing said substrate through a film interface on a solution and subsequently withdrawing said substrate from said solution with a layer at least partially comprised of protein or lipid matter attached to said substrate, said substrate being passed through the film interface on a solution a plurality of times to sequentially deposit biofilm layers on said substrate and form a biomembrane comprising a plurality of biofilm layers, said substrate being consecutively passed through two film interfaces, one of the film interfaces resulting in the deposition on said substrate of protein and lipid matter and the other of the film interfaces resulting in the deposition of lipid matter and cholesterol.

18. A method of testing a material without the use of animals to determine the potential of the material to harm human or animal tissue, said method comprising the steps of:

forming a biomembrane having at lest some constituent matter of human or animal tissue;

applying a quantity of material to said biomembrane;

maintaining said biomembrane and said quantity of material in contact for a period of time after applying said quantity of material to said biomembrane; and monitoring the condition of said biomembrane to detect any change in at least one physical characteristic of said biomembrane caused by said quantity of material during said period of time, said step of monitoring the condition of said biomembrane to detect any change in at least one physical characteristic of said biomembrane comprising measuring the thickness of said biomembrane to determine any change in thickness occurring during said period of time by a surface plasmon spectrometer, said surface plasmon spectrometer measuring change in the refractive index of the biomembrane.

19. The method according to claim 18 wherein change to the refractive index of the biomembrane is measured on a substantially continuous basis.

20. A method of testing a material without the use of animals to determine the potential of the material to harm human or animal tissue, said method comprising the steps of:

forming a biomembrane having at least some constituent matter of human or animal tissue;

applying a quantity of material to said biomembrane;

maintaining said biomembrane and said quantity of material in contact for a period of time after applying said quantity of material to said biomembrane;

monitoring the condition of said biomembrane to detect any change in at least one physical characteristic of said biomembrane caused by said quantity of material during said period of time, said step of forming said biomembrane comprising depositing at least one biofilm layer on a substrate, said at least one biofilm layer being at least partially comprised of protein or lipid matter and the step of depositing said at least one biofilm layer on said substrate including passing said substrate through a film interface on a solution and subsequently withdrawing said substrate from said solution with a layer at least partially comprised of protein or lipid matter attached to said substrate;

incorporating protein in said solution whereby protein is attached to said substrate in said at least one biofilm layer when said substrate is passed through the film interface on said solution;

providing a mixture of protein and lipid matter at said film interface whereby said at least one biofilm layer includes a mixture of protein and lipid matter; and adjusting the relative quantities of protein and lipid matter at said film interface to approximate different types of human or animal tissue.

21. A method of testing a material without the use of animals to determine the potential of the material to harm human or animal tissue, said method comprising the steps of:

forming a biomembrane having at least some constituent matter of human or animal tissue;

applying a quantity of material to said biomembrane;

maintaining said biomembrane and said quantity of material in contact for a period of time after applying said quantity of material to said biomembrane; and monitoring the condition of said biomembrane to detect any change in at least one physical characteristic of said biomembrane caused by said quantity of material during said period of time, said step of monitoring the condition of said biomembrane to detect any change in at least one physical characteristic of said biomembrane comprising measuring the index of refraction of said biomembrane to determine any change in the index of refraction during said period of time.

22. The method according to claim 21 wherein the changes in the index of refraction of said biomembrane are measured by a surface plasmon spectrometer using optical wave guide modes.

23. The method according to claim 21 wherein change in the index of refraction of said biomembrane is measured by a surface plasmon spectrometer using optical wave guide modes.

24. A method of testing a material without the use of animals to determine the potential of the material to harm human or animal tissue, said method comprising the steps of:

forming a biomembrane comprised of at least one biofilm layer by depositing at least one biofilm layer on a substrate, said at least one biofilm layer having physical characteristics of human or animal tissue and including at least some constituent matter of human or animal tissue;

applying a quantity of material to said biomembrane;

maintaining said biomembrane and said quantity of material in contact for a period of time after applying said quantity of material to said biomembrane; and monitoring the condition of the biomembrane during said period of time to detect any change in at least one physical characteristic of said biomembrane caused by said quantity of material during said period of time, said step of forming said biomembrane comprising depositing at least one biofilm layer on a substrate, at least one biofilm layer being at least partially comprised of protein or lipid matter and the step of depositing said at least one biofilm layer on said substrate including passing said substrate through a film interface on a solution and subsequently withdrawing said substrate from said solution with a layer at least partially comprised of protein or lipid matter attached to said substrate.

25. The method according to claim 24 wherein said substrate is passed through the film interface on a solution a plurality of times to sequentially deposit biofilm layers on said substrate and form a biomembrane comprising a plurality of biofilm layers.

26. The method according to claim 25 wherein said substrate is consecutively passed through two film interfaces, one of the film interfaces resulting in the deposition on said substrate of protein and lipid matter and the other of the film interfaces resulting in the deposition of lipid matter and cholesterol.

27. The method according to claim 24 wherein said solution is contained in a Langmuir-Blodgett trough and wherein said substrate is passed through the film interface on the solution in said Langmuir-Blodgett trough.

28. The method according to claim 24 including the step of incorporating protein in said solution whereby protein is attached to said substrate in said at least one biofilm layer when said substrate is passed through the film interface on said solution.

29. The method according to claim 28 including the step of incorporating cholesterol in said solution whereby cholesterol is attached to said substrate in said at least one layer when said substrate is passed through the film interface on said solution.

30. The method according to claim 28 including providing a mixture of protein and lipid matter at said film interface whereby said at least one biofilm layer includes a mixture of protein and lipid matter.

31. The method according to claim 30 including the step of adjusting the relative quantities of protein and lipid matter at said film interface to approximate different types of human or animal tissue.

32. The method according to claim 24 wherein said substrate has a hydrophobic surface and wherein said at least one biofilm layer is deposited on said hydrophobic surface.

33. The method according to claim 24 wherein said substrate has a hydrophilic surface and wherein said at least one biofilm layer is deposited on said hydrophilic surface.

* * * * *